United States Patent [19]

Garwood et al.

[11] Patent Number: 4,717,782

[45] Date of Patent: Jan. 5, 1988

[54] CATALYTIC PROCESS FOR OLIGOMERIZING ETHENE

[75] Inventors: William E. Garwood, Haddonfield, N.J.; John D. Kushnerick, Media, Pa.; Samuel A. Tabak, Wenonah, N.J.

[73] Assignee: Mobil Oil Corporation, New York, N.Y.

[21] Appl. No.: 893,522

[22] Filed: Aug. 5, 1986

Related U.S. Application Data

[63] Continuation-in-part of Ser. No. 775,906, Sep. 13, 1985, abandoned.

[51] Int. Cl.⁴ .............................................. C07C 2/02
[52] U.S. Cl. .................................... 585/531; 585/533; 585/255; 585/329
[58] Field of Search ............... 585/255, 329, 330, 319, 585/332, 517, 518, 531, 533; 208/46, 49

[56] References Cited

U.S. PATENT DOCUMENTS

| | | |
|---|---|---|
| 2,581,228 | 1/1952 | Bailey et al. . |
| 3,827,968 | 8/1974 | Givens et al. . |
| 4,150,062 | 4/1986 | Garwood et al. . |
| 4,211,640 | 7/1980 | Garwood et al. . |
| 4,433,185 | 2/1984 | Tabak . |
| 4,444,988 | 4/1984 | Capsuto et al. . |
| 4,497,968 | 2/1985 | Wright et al. .................. 585/304 |
| 4,511,750 | 4/1985 | Miller . |
| 4,517,396 | 5/1985 | Hoek et al. .................... 585/415 |
| 4,542,247 | 9/1985 | Chang et al. .................. 585/330 |
| 4,542,251 | 9/1985 | Miller ........................... 585/533 |
| 4,547,601 | 10/1985 | Holland et al. ............... 585/329 |
| 4,608,450 | 8/1986 | Miller . |

*Primary Examiner*—Andrew H. Metz
*Assistant Examiner*—Chung K. Pak
*Attorney, Agent, or Firm*—Alexander J. McKillop; Michael G. Gilman; L. G. Wise

[57] ABSTRACT

A continuous catalytic process for converting ethene-rich olefinic feedstock containing reducing gas to heavier liquid hydrocarbon product, comprising the steps of contacting the ethene-rich feedstock at elevated temperature in a catalytic reaction zone with a zeolite catalyst comprising a nickel-ethene oligomerization component and a shape-selective medium pore acid zeolite oligomerization component to convert at least a portion of the lower olefinic components to heavier olefinic hydrocarbons; and feeding water with the feedstock in sufficient amount to prevent substantial reduction of the nickel component.

14 Claims, 5 Drawing Figures

CATALYTIC PROCESS FOR OLIGOMERIZING ETHENE

RELATION TO COPENDING APPLICATION

This application is a continuation-in-part of copending U.S. patent application Ser. No. 775,906, filed Sept. 13, 1985, abandoned, incorporated herein by reference.

FIELD OF THE INVENTION

This invention relates to a catalytic technique for upgrading light olefin to heavier hydrocarbons. In particular, it provides a continuous process for oligomerizing ethene-rich olefinic feedstock to produce distillate- and gasoline-range liquid fuels or the like.

BACKGROUND OF THE INVENTION

Developments in zeolite catalysis and hydrocarbon conversion processes have created interest in utilizing olefinic feedstocks for producing $C_5^+$ gasoline, diesel fuel, etc. In addition to basic chemical reactions promoted by ZSM-5 type zeolite catalysts, a number of discoveries have contributed to the development of new industrial processes. These are significantly safe, environmentally acceptable processes for utilizing feedstocks that contain lower olefins, especially $C_2$–$C_5$ alkenes. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood, et al., have also contributed improved processing techniques, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5^+$ aliphatic and aromatic hydrocarbons. Product distribution for liquid hydrocarbons can be varied by controlling process conditions, such as temperature, pressure and space velocity. Gasoline ($C_5$–$C_9$) is readily formed at elevated temperature (e.g., up to about 400° C.) and moderate pressure from ambient to about 5500 kPa, preferably about 250 to 2900 kPa. Olefinic gasoline can be produced in good yield and may be recovered as a product or fed to a low severity, high pressure reactor system for further conversion to heavier distillate-range products. Distillate mode operation can be employed to maximize production of $C_{10}^+$ aliphatics by reacting the lower and intermediate olefins at high pressure and moderate temperature. Operating details for typical "MOGD" oligomerization units are disclosed in U.S. Pat. Nos. 4,456,779; 4,497,968 (Owen, et al.) and U.S. Pat. No. 4,433,185 (Tabak), incorporated herein by reference. At moderate temperature and relatively high pressure, the conversion conditions favor distillate-range product having a normal boiling point of at least 165° C. (330° F.). Lower olefinic feedstocks containing $C_2$–$C_6$ alkenes may be converted selectively; however, the low severity distillate mode conditions do not convert a major fraction of ethene. While propene, butene-1, and others may be converted to the extent of 50% to 95% in the moderate temperature distillate mode, only about 10% to 30% of the ethene component will be converted using HZSM-5 or similar acid zeolites. Many feedstocks of commercial interest, such as FCC offgas, dehydrogenation products, ethane cracking, etc., contain both ethene and hydrogen along with $H_2S$ and light aliphatics. Ethene can be converted at moderately elevated temperature with a bifunctional nickel zeolite catalyst. However, it has been found that the presence of reducing gas in the feedstock would inactivate the nickel oligomerization component, thus decreasing the yield of $C_3^+$ hydrocarbon products.

SUMMARY OF THE INVENTION

It has been discovered that ethene can be oligomerized by contacting an ethene-rich feedstock with a bifunctional metallic zeolite in the presence of a reducing component, such as hydrogen, by cofeeding an amount of water to effectively maintain selectivity of the metallic oligomerization component. Moreover, said water is present in amount sufficient to maintain the nickel component of the oligomerization catalyst in an oxidized state. Accordingly, it is an object of the present invention to convert a gas stream containing ethene in the presence of hydrogen to liquid hydrocarbons.

DESCRIPTION OF PREFERRED EMBODIMENTS

Figure 1:
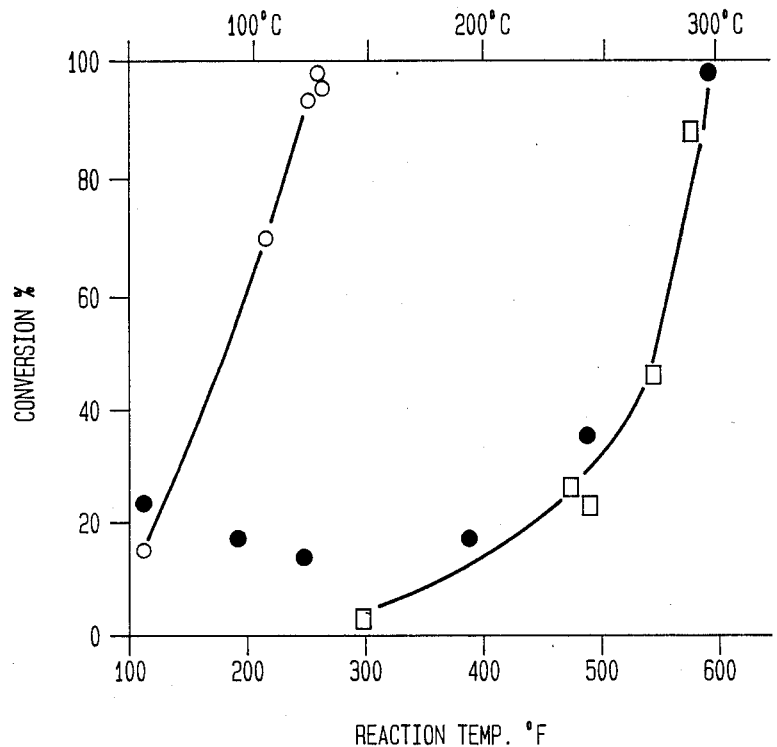
FIG. 1 is a graphic plot of ethene conversion using different catalysts.

The catalyst materials include two catalytic components: (1) a metallic oligomerization component, such as ionic $Ni^{+2}$, and (2) a shape-selective medium pore acidic oligomerization catalyst, such as ZSM-5 zeolite. These components may be present in admixture or combined in a unitary bifunctional solid particle. In a preferred embodiment, a metal ion-exchanged zeolite, such as Ni-ZSM-5, is employed; however, it is possible to use metal-impregnated supported catalyst with metal oxide, or ionically associated components, or a catalyst composed of an admixture of a zeolite with a metal (impregnated or exchanged) containing support. It is preferred to utilize an ethene dimerization metal or oligomerization agent to effectively convert at least 30% of feedstock ethene in a continuous reaction zone under moderate process conditions. Ethene conversion metallic catalysts are disclosed in U.S. Pat. Nos. 2,581,228, 4,511,750 and European Patent Application No. 133,052.

The oligomerization catalysts preferred for use herein include the medium pore (i.e., about 5-7Å) shape-selective crystalline aluminosilicate zeolites having a silica-to-alumina ratio of at least 12, a constraint index of about 1 to 12 and acid cracking activity of about 10-250. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245 and 4,046,839; 4,414,423; 4,417,086; 4,517,396 and 4,542,251. The disclosures of these patents are incorporated herein by reference. It is advantageous to employ a standard ZSM-5 having a silica alumina molar ratio of about 70:1, suitably modified. A typical zeolite catalyst component having Bronsted acid sites may consist essentially of aluminosilicate ZSM-5 zeolite with 35 wt.% alumina binder in the form of cyclindrical extrudates of about 1-5 mm diameter. These siliceous zeolites may be employed in their acid forms or ion exchanged with one or more suitable metal cations, such as Ni, Co and/or other metals of Periodic Groups III to VIII. Other catalysts which may be employed for converting lower olefins include the gallosilicate, borosilicate, ferrosilicate, "silicalite", and/or synthetic mordenite materials.

In this description, metric units and parts by weight are employed unless otherwise stated. Various reactor configurations may be used, including fluidized bed catalytic reactors, moving bed and fixed bed reactors.

The preferred feedstock comprises $C_2$-$C_6$ olefins including at least 5 mole % ethene. Non-deleterious components, such as paraffins and inert gases, may be present. A particularly useful feedstock is a light gas by-product of FCC gas oil cracking units containing typically 10-40 mol % $C_2$-$C_4$ olefins and 5-35% $H_2$ with minor amounts of $C_1$-$C_4$ paraffins and $N_2$.

In a typical process, the ethylene-rich $C_2$+olefinic feedstock is converted in a catalytic reactor under oligomerization conditions and moderate pressure to produce $C_5$+hydrocarbons rich in gasoline-range olefins and aromatics. Light gas, including unreacted ethylene, may be recovered from the product stream in a separation unit and recycled to the reactor. It is within the inventive concept to cascade a major amount of condensed $C_5$+hydrocarbons from the primary stage into a second distillate mode reactor. This will advantageously maximize distillate production by polymerizing gasoline boiling-range components. Because the primary ethene conversion stage is preferably operated at a pressure level of about 200-3600 kPa, the compression requirements are efficient. A condensed intermediate liquid stream may be brought to higher pressure in a second catalytic reactor zone by pumping prior to contacting a second catalyst bed for further conversion to $C_{10}$+distillate range product. Gasoline rich in $C_5$-$C_9$ olefins may be recovered from the second separation zone or recycled to the distillate mode reactor zone.

ETHENE REACTOR OPERATION

A typical reactor unit employs an adiabatic catalyst zone with adjustable gas recycle, whereby the reaction exotherm can be carefully controlled to prevent excessive temperature above the usual operating range of about 100° C. to 450° C., preferably at average reactor temperature of 250° C. to 400° C. Energy conservation in the MOGD system utilizes at least a portion of the reactor exotherm heat value by exchanging hot reactor effluent from one or more reactors with feedstock and/or recyle stream. Optional heat exchangers may recover heat from the effluent stream prior to fractionation. It is preferred to operate the ethene conversion reactors at moderate pressure of about 200 to 3600 kPa (15-500 psig).

The reactor system may contain multiple downflow adiabatic catalytic zones in each reactor vessel. The weight hourly space velocity (WHSV, based on total olefins in the fresh feedstock) is about 0.1-2 WHSV. In this mode, the molar recycle ratio for light gas is at least equimolar, based on total olefins in the fresh feedstock. The preferred molar ratio of recycle to fresh feedstock olefin is at least 2:1. Typical product fractionation systems are described in U.S. Pat. Nos. 4,456,779 and 4,504,693 (Owen, et al.).

EXAMPLES 1-3

In order to demonstrate the improvement in ethene conversion using a bifunctional catalyst, a series of comparative runs are conducted in a fixed bed tubular reactor. The unexchanged HZSM-5 catalyst is a standard aluminosilicate zeolite having an acid value of about 180, a silica-to-alumina ratio of 70:1, and crystalline size of about 0.02 to 0.05 microns. The catalyst is prepared as an extrudate having a particle size of 14 to 25 mesh size (U.S.G.) with 35 wt. % alumina binder. The calcined acid form of HZSM-5 is at least partially ion-exchanged with nickel ($Ni^{+2}$) and recalcined to produce a bifunctional catalyst containing about 1 wt. % Ni. To show how the preferred nickel-treated ZSM-5 catalyst is affected by metal valence state, comparative runs are made in which the nickel ion-exchanged ZSM-5 is treated in a reducing atmosphere. The graphic plot in FIG. 1 compares conversion of ethylene over HZSM-5 0.9% Ni-ZSM-5 (ionically exchanged) and reduced nickel catalyst. The reduced nickel ($Ni^o$) produced by calcining the exchanged Ni-ZSM-5 at 480° C. in hydrogen instead of nitrogen, thus providing a material in which the major amount of nickel is present in the reduced metallic state. While the reduced catalyst has significant activity initially, it decreases rapidly as temperature is increased during the run, approaching the lower activity of HZSM-5.

The conversion of ethene ($C_2=$) using HZSM-5 catalyst requires excessively high temperature, above 280° C., to obtain more than 50% conversion, thus increasing aromatics yield. By contrast, the acidic Ni-ZSM-5 bifunctional catalyst converts a major amount of ethene at moderate temperature.

EXAMPLES 4-6

Continuous runs are made in a larger scale reactor unit employing standard ZSM-5 (65%) extrudate catalyst at elevated pressure. Example 4 employs HZSM-5 having an acid cracking activity (alpha value) of about 200. Examples 5 and 6 employ nickel-exchanged (0.9 wt.%) acid ZSM-5. The fresh feedstock for Examples 4 and 6 contain 12.6 mol % ethene ($C_2=$), 7.9% propene ($C_3=$) 53.6% $N_2$ and 25.9% $H_2$. In Example 5, the propene is replaced with $N_2$ (total of 61.5% $N_2$ in feed). These experimental runs are conducted at similar conversion rates and show the yields for each run. The results of these runs are set forth in Table I.

TABLE 1

| Example | 4 | 5 | 6 |
|---|---|---|---|
| Days on stream | 7.5 | 7.3 | 15.5 |
| OPERATING CONDITIONS | | | |
| WHSV on HC feed, 1/hr. | 1.00 | 0.98 | 0.56 |
| Reactor Pressure, KPA | 1825 | 1825 | 3204 |
| Gas recycle ratio, MOL/MOL | 2.0 | 2.0 | 2.0 |
| Avg reactor temp., °C. | 376 | 261 | 286 |
| Reactor 1 inlet, °C. | 321 | 176 | 215 |
| T, °C. | 75 | 183 | 147 |
| $C_2 =$ PP at RXT inlet, KPA | 87.6 | 106.4 | 165.0 |
| $C_3 =$ PP at RXT inlet, KPA | 33.6 | 49.4 | 4.1 |
| Mole $H_2O$/mole $H_2$ at reactor inlet | 0.0 | 0.3 | 0.3 |
| Propane/Propene Ratio (RI) | 1.13 | 1.14 | 1.20 |
| YIELDS ON HYDROCARBON, WT % | | | |
| $C_5$+ including alkylate | 82.3 | 75.4 | 72.1 |
| potential alkylate | 9.3 | 9.4 | 10.4 |
| $C_4$+ | 86.1 | 79.2 | 73.1 |
| $C_5$+ | 73.0 | 66.0 | 61.7 |
| $C_5$'s | 14.8 | 13.3 | 10.8 |
| $NC_4$ | 1.7 | 1.7 | 1.6 |

TABLE 1-continued

| Example | 4 | 5 | 6 |
|---|---|---|---|
| $IC_4$ | 4.8 | 4.8 | 5.4 |
| $C_4=$ | 6.6 | 6.7 | 4.3 |
| $C_3$ | 2.8 | 2.4 | 2.3 |
| $C_3=$ | 2.5 | 2.1 | 1.9 |
| $C_2$ | 0.6 | 7.1 | 10.4 |
| $C_2=$ | 8.0 | 9.2 | 12.3 |
| $C_1$ | 0.1 | 0.0 | 0.0 |
| CONVERSION, WT % | | | |
| $C_2=$ | 83.7 | 84.0 | 87.7 |
| $C_3=$ | 94.7 | 95.2 | 0.0 |
| Total feed olefin | 89.0 | 88.9 | 87.7 |
| PRODUCT PROPERTIES | | | |
| Raw octane, R + O | 93.1 | — | 89.8 |
| Raw Octane, M + O | — | — | — |
| S.G. at 15.6° C. | 0.734 | 0.736 | 0.750 |
| D2887 B.P. DISTRIBUTION, °C. | | | |
| 5 | — | 18 | 22 |
| 10 | — | 35 | 40 |
| 30 | — | 73 | 91 |
| 50 | — | 109 | 123 |
| 70 | — | 139 | 151 |
| 90 | — | 181 | 188 |
| 95 | — | 201 | 201 |
| 99.5 | — | 268 | 263 |

Figure 2:
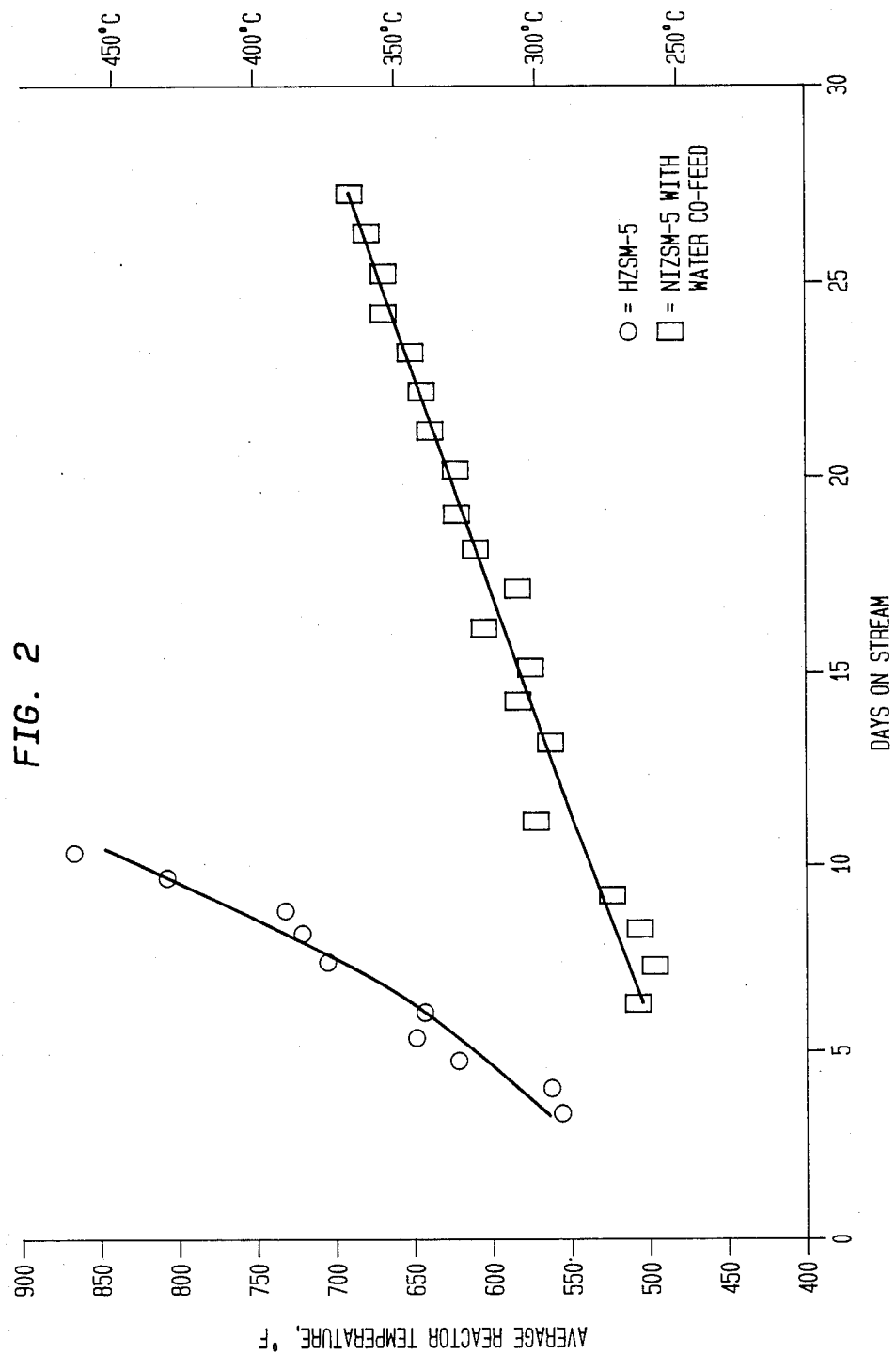
FIGS. 2 and 3 plot reactor temperature vs. time.
Figure 3:
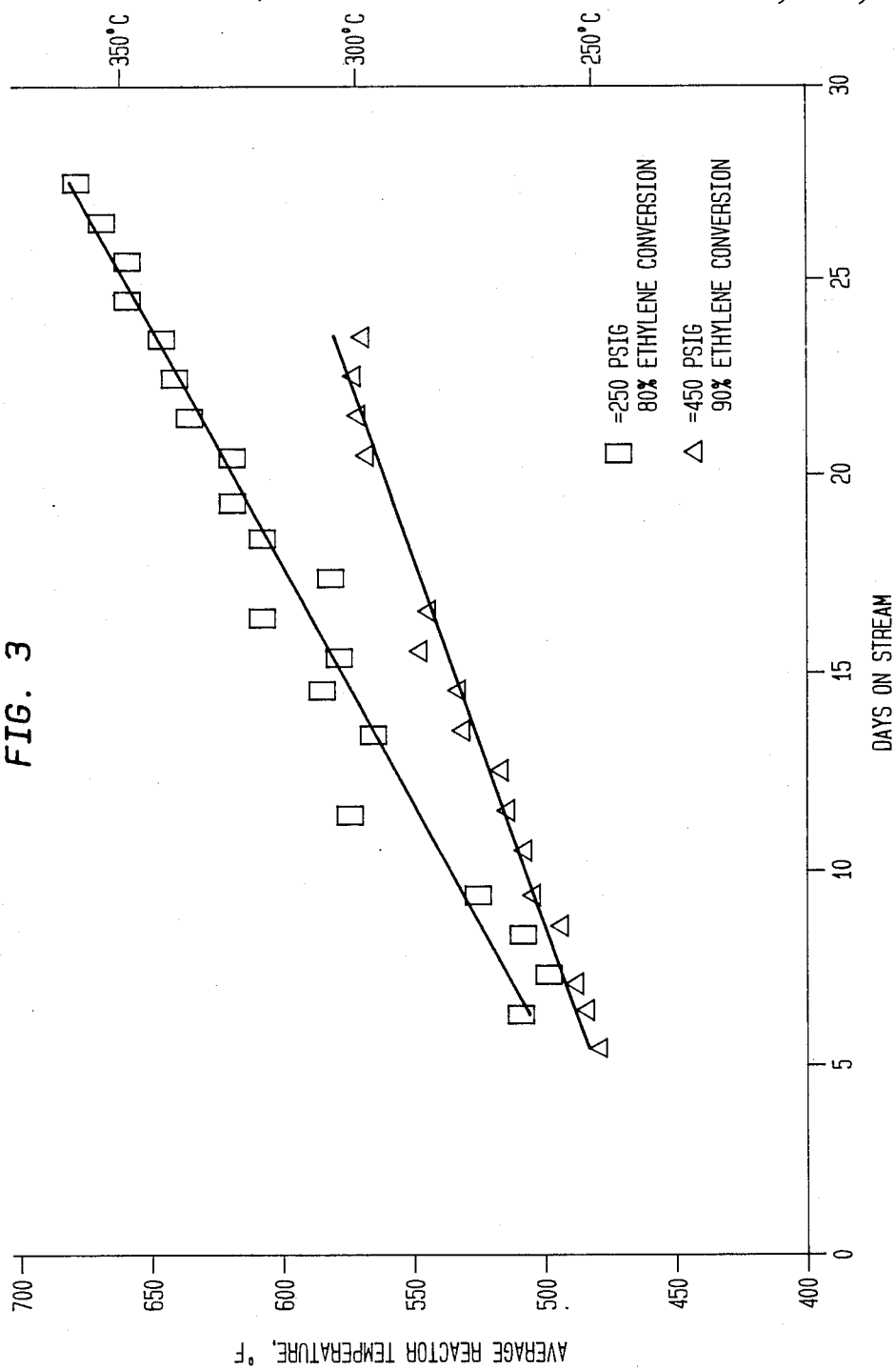

These examples are depicted graphically in FIGS. 2 and 3 for long-term, continuous runs. FIG. 2 shows the advantage of NiZSM-5 with water cofeed over HZSM-5. Catalyst deactivation rate is reduced by about a factor of 5. These average reactor temperatures are normalized to 80% ethylene conversion. FIG. 3 shows the advantage of operating at increased pressures. By raising total pressure from 1825 kPa (250 psig) to 3200 kPa (450 psig), it is possible to operate at 10% higher ethylene conversion and still further reduce catalyst deactivation rate by about a factor of 1.5. The average reactor temperatures for the 450 psig experiment have been normalized to a constant 90% ethylene conversion.

Figure 4:
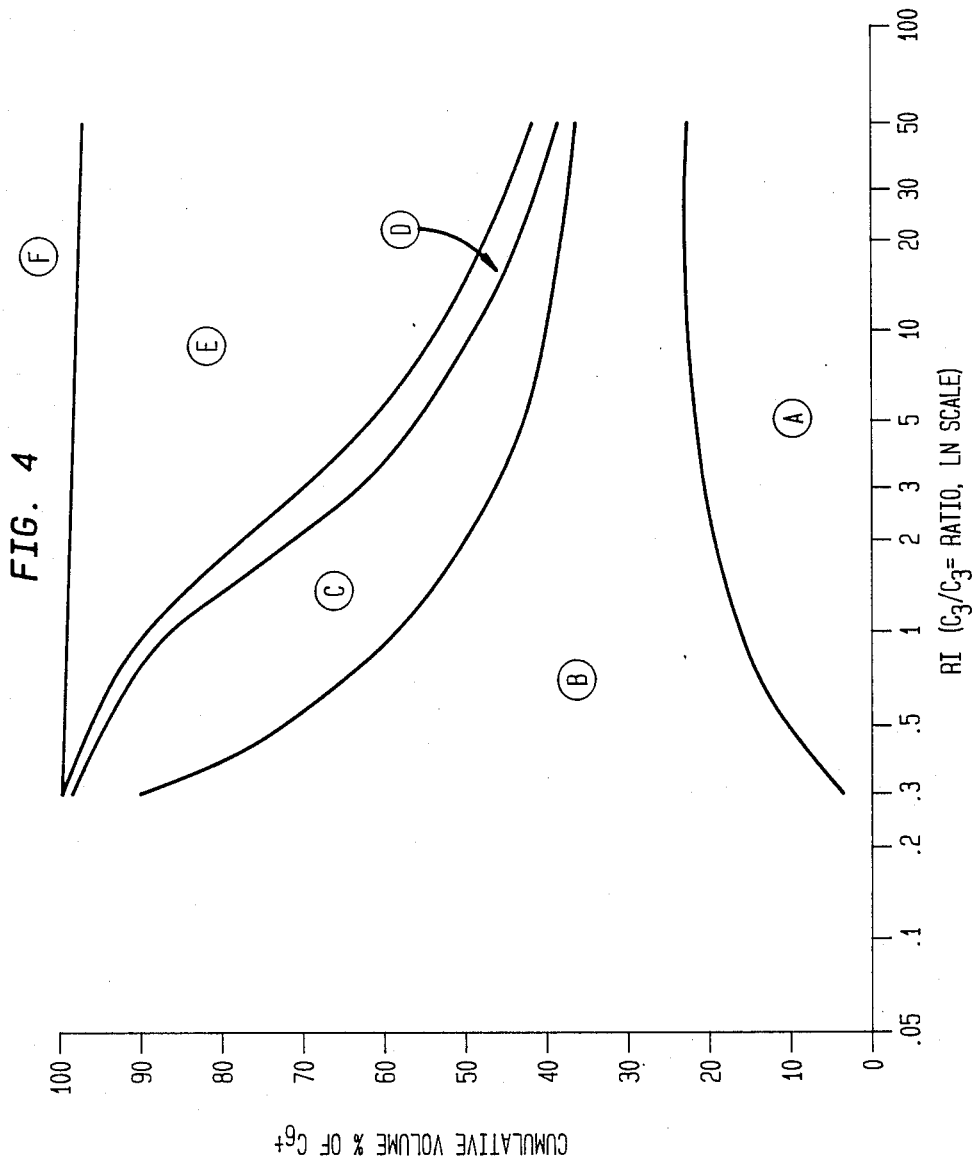
FIG. 4 plots liquid product composition vs. catalyst activity.

FIG. 4 is a semi-log plot depicting product distribution and shows how the composition of the $C_6+$ gasoline product changes as processing severity increases. Severity is indicated by RI, the weight ratio of propane to propene in the unit's product. Hydrocarbon class zones are indicated by letters, which represent the following:

| Zone | Formula | Hydrocarbon Type |
|---|---|---|
| A | $C_nH_{2n+2}$ | Paraffin |
| B | $C_nH_{2n}$ | Olefin or Naphthene |
| C | $C_nH_{2n-2}$ | Cyclo-olefin or di-olefin |
| D | $C_nH_{2n-4}$ | Cyclo-diolefin or Tri-olefin |
| E | $C_nH_{2n-6}$ | Aromatic |
| F | $C_nH_{2n-8}$ | Multi-cyclic |

Figure 5:
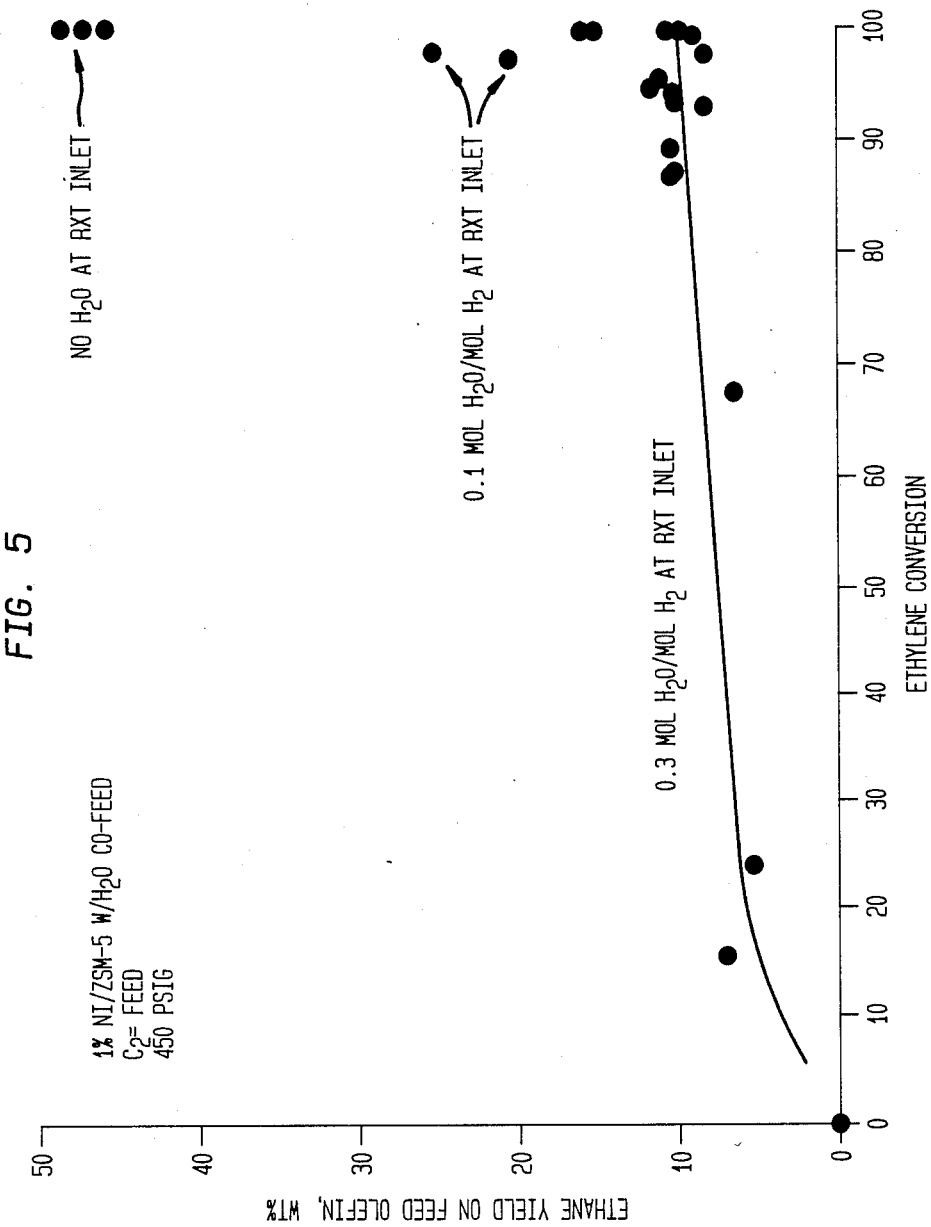
FIG. 5 shows effect of water cofeedings.

FIG. 5 graphically depicts the effect of water cofeeding selectivity in Example 6. This plot shows that with NiZSM-5, water cofeed is required to maintain selectivity to higher molecular weight product. Without the water, ethylene hydrogenation becomes significant. These data are set forth in Table II following:

TABLE II
Reversible Effect of Water Removal

| Example | 6 With $H_2O$ | 7 $H_2O$ Removed | 8 $H_2O$ Restored |
|---|---|---|---|
| Time on stream (days) | 16.5 | 17.5 | 20.5 |
| $H_2O/H_2$ mol/mol | 0.3 | 0.0 | 0.3 |
| (reactor inlet) Ethane Yield on Olefin, Wt % | 10.7 | 48.6 | 11.7 |
| $C_5+$ Yield on Olefin, Wt % | 62.7 | 16.8 | 62.9 |
| $C_2=$ Conversion | 90.1 | 99.9 | 95.5 |
| Average Reactor Temperature °C./(°F.) | 285(544) | 297(567) | 299(570) |
| RI (reaction severity index) | 1.43 | 67.75 | 2.54 |

These examples show that catalyst selectivity changes are reversible as water is removed from and returned to the reactor.

While the invention has been described by specific examples and embodiments, there is no intent to limit the inventive concept except as set forth in the following claims.

We claim:

1. A catalytic process for converting ethene-rich lower olefinic feedstock containing hydrogen heavier liquid hydrocarbon product, comprising the steps of contacting said ethene-rich feedstock containing hydrogen at elevated temperature of about 100° to about 450° C. in the presence of water with at least one conversion catalyst comprising a nickel ethene oligomerization component and a shape-selective medium pore acidic zeolite oligomerization component to convert at least a portion of the feedstock to said heavier hydrocarbon product, said water being present in amount sufficient to maintain the nickel component in an oxidized state.

2. The process of claim 1 wherein the feedstock comprises at least 5 mol % ethene and the nickel ethene oligomerization component comprises ion-exchanged nickel.

3. The process of claim 1 wherein the feedstook consists essentially of $C_2$-$C_4$ olefins, $C_1$-$C_4$ paraffins and hydrogen, and the catalyst consists essentially of acidic Ni-ZSM-5.

4. The process of claim 1 wherein the catalyst consist essentially of $Ni^{+2}$ and ZSM-5, and said water has been fed concurrently in a molar rate of at least 0.1 moles per mole of hydrogen.

5. The process of claim 1 wherein the acidic zeolite oligomerization component consists essentially of a crystalline aluminosilicate zeolite having a silica-to-alumina molar ratio greater than 12 and a constraint index of about 1 to 12, and wherein the zeolite is ion exchanged with at least one Group VIII metal.

6. The process of claim 1 wherein the feedstock comprises at least 5 mole % ethene.

7. A process for oligomerizing olefinic feedstock containing ethylene and hydrogen by contacting the feedstock under oligomerization conditions with a bi-functional solid catalyst having a nickel ethylene oligomerization component and an acidic shape-selective crystalline zeolite component, and comprising the step of contacting the catalyst with water during said oligomerizing in sufficient amount to maintain the nickel component in an oxidized state.

8. The process of claim 7 wherein the nickel component comprises a major portion $Ni^{+2}$ and wherein a sufficient amount of water is fed concurrently with hydrogen to maintain the Ni predominantly in said ionic state.

9. The process of claim 8 wherein the bifunctional catalyst consists essentially of Ni-ZSM-5.

10. The process of claim 9 wherein the catalyst has an acid value of about 1 to 200.

11. The process of claim 7 wherein the bifunctional catalyst converts at least 50% of ethylene in the feedstock in a continuous fixed bed process at a pressure not greater than about 3600 kPa at a temperature of at least 100° C.

12. A process for oligomerizing an ethylene-containing olefinic feedstock containing a minor amount of reducing gas to heavier hydrocarbons by contacting said ethylene-containing olefinic feedstock containig a minor amount of reducing gas with a solid nickel and zeolite containing catalyst at elevated oligomerizing temperature, comprising feeding water concurrently, with the feedstock in the amount of at least 0.1 water equivalents per molar equivalent of said reducing gas, thereby maintaining at least a portion of the catalytic nickel of the solid nickel and zeolite containing catalyst in an active oxidized state for oligomerization.

13. The process for oligomerizing said feedstock according to claim 12 wherein the feedstock contains at least about 5 mole percent ethene, up to 2 moles hydrogen per mole of ethene, and at least 0.1 mole of water in the form of steam per mole of hydrogen.

14. The process for oligomerizing said feedstock according to claim 13, wherein the elevated oligomerizing temperature is about 100° C. to 450° C. and wherein ethene partial pressure is about 50 to 1000 kPa.

* * * * *